US007675295B2

(12) United States Patent
Materer et al.

(10) Patent No.: US 7,675,295 B2
(45) Date of Patent: Mar. 9, 2010

(54) PASSIVE WIRELESS CORROSION SENSOR

(75) Inventors: Nicholas F. Materer, Stillwater, OK (US); Allen W. Apblett, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 236 days.

(21) Appl. No.: 11/850,496

(22) Filed: Sep. 5, 2007

(65) Prior Publication Data

US 2009/0058427 A1 Mar. 5, 2009

(51) Int. Cl.
*G01R 27/00* (2006.01)

(52) U.S. Cl. .................. 324/649; 324/76.11; 343/867

(58) Field of Classification Search ............... 324/700, 324/71.2, 649, 76.1; 340/601; 205/775.5; 343/866, 867
See application file for complete search history.

(56) References Cited

U.S. PATENT DOCUMENTS

| | | | |
|---|---|---|---|
| 3,716,460 A * | 2/1973 | Weisstuch et al. ........ 205/775.5 |
| 4,677,373 A | 6/1987 | Kobayashi et al. |
| 5,122,330 A | 6/1992 | Solomon et al. |
| 5,338,432 A | 8/1994 | Agarwala et al. |
| 5,446,369 A | 8/1995 | Byrne et al. |
| 6,805,788 B1 | 10/2004 | Gonzalez-Martin et al. |
| 6,806,808 B1 | 10/2004 | Watters et al. |
| 6,894,512 B2 * | 5/2005 | Girshovich et al. ........ 324/694 |
| 6,911,828 B1 | 6/2005 | Brossia et al. |
| 2004/0113790 A1 | 6/2004 | Hamel et al. |
| 2006/0002815 A1 | 1/2006 | Harris et al. |
| 2006/0125493 A1* | 6/2006 | Subramanian et al. ...... 324/700 |

FOREIGN PATENT DOCUMENTS

| JP | 1296156 | 11/1989 |
|---|---|---|
| JP | 2000304684 | 11/2000 |

OTHER PUBLICATIONS

PCT International Search Report, International Application PCT/US2008/074340, mailed Feb. 25, 2009.
PCT Written Opinion of the ISA, International Application PCT/US2008/074340, mailed Feb. 25, 2009.

* cited by examiner

*Primary Examiner*—Vincent Q Nguyen
(74) *Attorney, Agent, or Firm*—Fellers, Snider, Blankenship, Bailey & Tippens

(57) ABSTRACT

A passive wireless corrosion sensor is disclosed. A circuit is configured to provide a signal response when energized. An antenna is configured to wirelessly receive energy for energizing the circuit and to receive the signal response from the circuit and transmit the signal response. A corrosion sensitive connector interposes the circuit and the antenna. The corrosion sensitive connector conducts the energy from the antenna to the circuit and conducts the signal response from the circuit to the antenna when in a substantially non-corroded state. The corrosion sensitive connector creates an effectively non conducting link between the antenna and the circuit when in a substantially corroded state.

8 Claims, 3 Drawing Sheets

US 7,675,295 B2

PASSIVE WIRELESS CORROSION SENSOR

FIELD OF THE INVENTION

This disclosure relates generally to corrosion sensors. More particularly, but not by way of limitation, this disclosure relates to wireless corrosion sensors, systems, and methods.

BACKGROUND OF THE INVENTION

Almost every man made construction is subject to corrosive forces. Corrosion affects aircraft, trains, automobiles, pipelines, factories, and a host of other devices, buildings, structures, and apparatus. In the United States alone, costs associated with policing and repair of corrosion runs into the hundreds of billions of dollars. Industrial segments including transportation, utilities, production and manufacturing, governments, and other infrastructure have a need to detect corrosion prior to significant damage occurring to the structure of interest In some instances, the cost to repair damages due to corrosion will be greater than half of the original costs to build the structure. These costs are exclusive of the other costs associated with the loss of use of a corroded structure such as loss production and capacity. Moreover, in some instances, environmental impacts are to be considered such as with the corrosion of an oil pipeline or another structure containing toxic or otherwise harmful materials.

What is needed is a system and method of addressing the above, and related, issues.

SUMMARY OF THE INVENTION

The present invention disclosed and claimed herein, in one aspect thereof comprises a passive wireless corrosion sensor. The sensor includes a circuit configured to provide a signal response when energized and an antenna configured to receive energy for energizing the circuit. The antenna receives the signal response from the circuit and transmits the signal response. A corrosion sensitive connector interposes the circuit and the antenna. The corrosion sensitive connector conducts the energy from the antenna to the circuit and conducts the signal response from the circuit to the antenna when in a substantially non-corroded state. The corrosion sensitive connector creates an effectively non conducting link between the antenna and the circuit when in a substantially corroded state.

In another embodiment disclosed herein the corrosion sensitive connector substantially prevents conduction of energy from the antenna to the circuit and substantially prevents conduction of the signal response from the circuit to the antenna when in a substantially non-corroded state.

In another embodiment an integrated circuit is powered by the interrogation signal from the antenna. A plurality of corrosion sensitive connectors is connected to the integrated circuit. In response to the interrogation signal the integrated circuit provides a continuity test of each of the plurality of corrosion sensitive connectors and provides a response back through the antenna indicative of the continuity test results.

The present invention disclosed and claimed herein in another aspect thereof comprises a method of modeling corrosion of a test object. The method includes applying one or more passive wireless corrosion sensors to a test object in locations where corrosion is monitored. The method includes wirelessly energizing the plurality of passive wireless corrosion sensors, and receiving a plurality of signal responses from the plurality of passive wireless corrosion sensors.

DETAILED DESCRIPTION OF THE PREFERRED EMBODIMENTS

Figure 1:
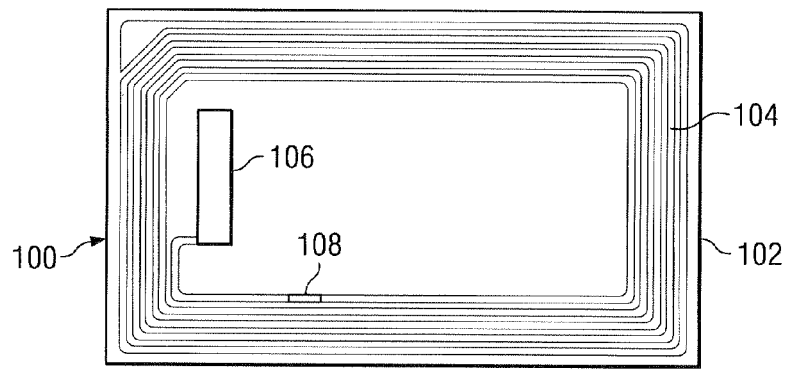
FIG. 1 is a schematic diagram of a passive wireless corrosion sensor according to aspects of the present disclosure.

Referring now to FIG. 1, a schematic diagram of a passive wireless corrosion sensor is shown. The sensor 100 is passive in that it does not contain a power source and is inactive until energized by radiofrequency, magnetic, or microwave energy, or other wireless energy fields. In the present embodiment, the sensor 100 is based upon radio frequency identification (RFID). The sensor 100 may be based upon a commercially available RFID tag or may be specifically made as described herein. The sensor 100 has a substrate or covering 102. The covering 102 may be plastic, Mylar®, rubber, or another suitable material. Contained within the covering 102 is the antenna 104. The antenna 104 is connected to a circuit 106 via a corrosion sensitive link or connector 108. The antenna 104 will be used to receive radiofrequency energy, magnetic energy, or other wireless energy that will be used to energize or power the circuit 106. It can be seen that the corrosion sensitive connector 108 interposes the antenna 104 and the circuit 106. All or a portion of the corrosion sensitive connector 108 will be exposed to the ambient environment such that the corrosiveness of the environment and/or the actual corrosion of a test object can be detected.

As is known in RFID technology, the antenna 104 will be used to receive wireless energy from an outside source. The energy may be stored within the circuit 106, possibly within a capacitor. When energized, the circuit 106 is capable of returning a signal back through the antenna 104. In some embodiments, the circuit 106 may be capable of returning only a signal to indicate that the circuitry 106 and the corrosion sensor 100 is functioning properly. In other embodiments, the circuit 106 may return an identification number that may be unique to the sensor 100 being read. In further embodiments, the circuit 106 may contain an electrically erasable programmable read-only memory (EEPROM) that may be capable of storing data as well.

As can be seen from FIG. 1, the sensor 100 may only be capable of returning a confirmation or identification signal while the corrosion sensitive connector 108 remains substantially intact. Because the corrosion sensitive connector 108 is exposed to the environment, it will be able to detect the cumulative effects of corrosive forces within the environment. When the corrosion sensitive connector 108 becomes substantially corroded such that it is no longer conductive, the sensor 100 will fail to respond to interrogation. It can be seen that without the corrosion sensitive connector 108 being substantially intact, the sensor 100 will be unable to return a signal because the circuit 106 no longer has a means of being powered nor a way to transmit a confirmation signal or identification number back. When the corrosion sensitive connector 108 is substantially corroded, the antenna 104 is essentially insulated from the circuit 106.

Figure 2A:
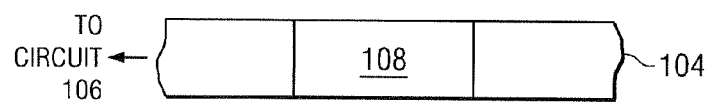
FIG. 2a is a close up cutaway view of the antenna and corrosion sensitive connector of FIG. 1 with the corrosion sensitive connector substantially intact.
Figure 2B:
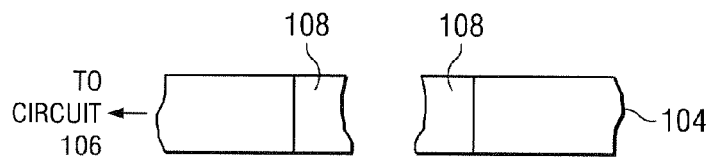
FIG. 2b is a close up cutaway view of the antenna and corrosion sensitive connector of FIG. 1 with the corrosion sensitive connector substantially corroded and open.

Referring now to FIG. 2a, a close up cutaway view of the antenna 104 and corrosion sensitive connector 108 is shown. As can be seen here, the corrosion sensitive connector 108 is required for continuity between the antenna 104 and the circuit 106. The drawing of FIG. 2a illustrates the corrosion sensitive connector 108 in a substantially intact configuration. That is, the corrosion sensitive connector 108 is largely corrosion free. Referring now to FIG. 2b, the corrosion sensitive connector 108 is illustrated in a substantially corroded state. It can be seen here that the corrosion sensitive connector 108, due to its exposure to the corrosive environment, has corroded to the point that continuity no longer exists between the antenna 104 and the circuit 106.

The material comprising the corrosion sensitive connector 108 may be chosen according to the underlying material of the test object. For example, if a sensor is employed to detect corrosion within a pipeline, the corrosion sensitive connector 108 should be made of a material substantially similar to that of the pipeline. In one embodiment, the sensor 100 could be applied to such a pipeline in between the primer and paint layers. It will be appreciated that the corrosion sensors 100 can be utilized to detect corrosion within and throughout a number of other structures.

Monitoring corrosion can help ensure structural integrity, reduce the risk of fatigue failures, and provide non destructive engineering test data, among other uses. By way of example and not by limitation, applications for the wireless passive corrosion sensors 100 include highways and bridges, pipelines, waterways and ports, hazardous materials storage, airports and aircraft, and railroads. The corrosion sensor 100 may be placed in any location where corrosion is a concern. In this way, corrosion may be detected before it becomes problematic and without substantial dismantling of the structure being monitored.

In addition to choosing a specific material for the corrosion sensitive connector 108 that is reflective of the corrosion sensitivity of the test object, the thickness of the material may also be chosen to reflect the degree of corrosion that is noteworthy with regards to the test object. The corrosion sensitive connector 108 may be varied in thickness to account for the degree of corrosion on the test object at which the sensor 100 should detect corrosion. In the present embodiment, the sensor 100 is binary. That is, the sensor 100 will be reflective only of whether or not corrosion has occurred and not necessarily the degree of corrosion. Hence, the thickness of the corrosion sensitive connector 108 may be utilized to ensure that corrosion is detected at the point desired by the end user.

In some embodiments the corrosion sensitive connector 108 will range from about 0.5 μm up to about 1 mm. Some thicknesses of the corrosion sensitive connector may be constructed from thin wire or foil comprised of the appropriate material. In other embodiments, the corrosion sensitive connector may be deposited into place using techniques such as chemical vapor deposition or other deposition techniques. Some embodiments will provide a corrosion sensitive connector 108 of the thinnest degree possible that is able to maintain circuit continuity. In these embodiments, the slightest degree of corrosion will register using the sensor 100.

It will be appreciated that the RFID tags of the present disclosure could be based in part on commercially available RFID tags. Many off the shelf RFID tags encase the antenna and other circuitry in a protective covering. In FIG. 1, this corresponds to the cover 102. The covering could be plastic, polymer or any other suitably resilient material. In one embodiment, the sensor 100 could be constructed by mechanically removing or opening a portion of the cover and a portion of the antenna link material and replacing it with the corrosion sensitive connector 108. Acid etching of the cover to provide access to modify the internal components is also a possibility. In one embodiment, the sensor 100 will be constructed from a Tag-it™ HF Transponder Inlay Rectangle—Large, Part Number RI-I02-110A, available from Texas Instruments Incorporated of Dallas, Tex.

Figure 3:
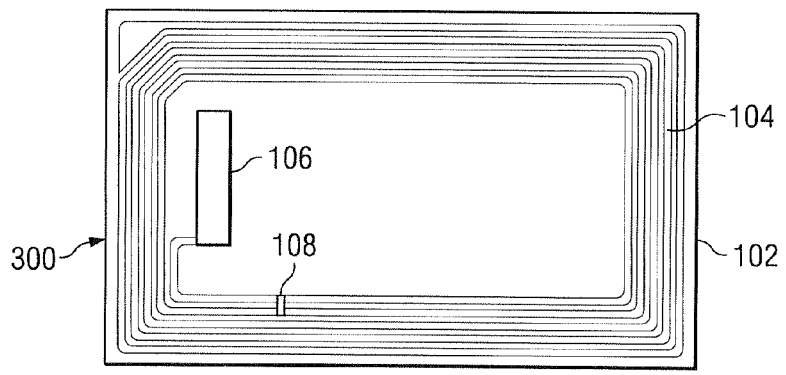
FIG. 3 is another embodiment of a wireless corrosion sensor according to aspects of the present disclosure.

Referring now to FIG. 3, another embodiment of a wireless corrosion sensor is illustrated. In the embodiment of FIG. 3, the corrosion sensor 300 is designed to remain non-operative until corrosion has been detected. As before, a cover 102 is provided, as well as an antenna 104, a circuit 106 and a corrosion sensitive connector 108. In the embodiment of FIG. 3, however, it can be seen that the corrosion sensitive connector 108 has been placed in a position to short the antenna 104. In this way, regardless of whether or not the antenna 104 is energized from an outside source, it will not be capable of transmitting the energy into the circuit 106. Upon corrosion of the corrosion sensitive connector 108, the corrosion sensitive connector 108 will no longer be able to short the antenna 104. At this time, the sensor 300 will operate as was previously described. Thus, only after corrosion of the corrosion sensitive connector 108 has occurred will the sensor 300 be active. As described, the sensor 300, when active, may be able to transmit a confirmation signal which may include an identification number and possibly other data. The other data may include, for example, the date that the sensor 300 was installed, the precise location of the sensor, the composition of the corrosion sensitive connector 108, and/or other pertinent information.

Figure 4:
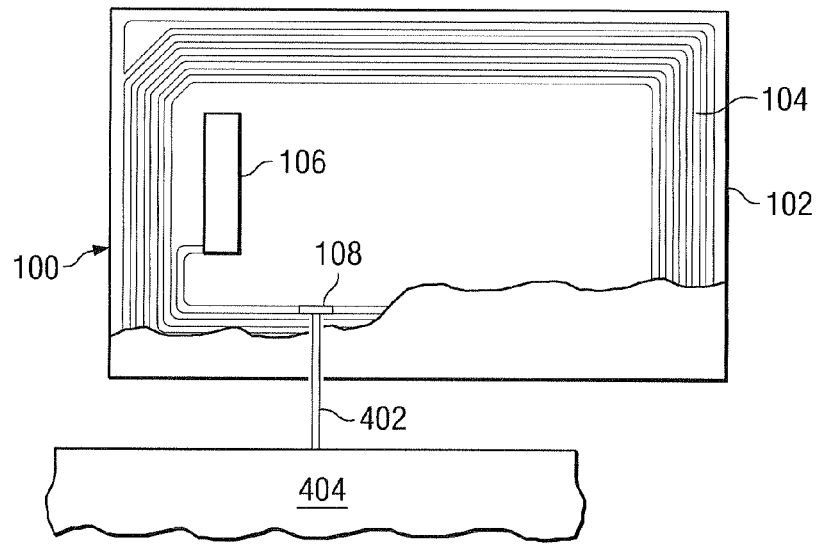
FIG. 4 is a schematic diagram of the corrosion sensor of FIG. 1 in a configuration to detect galvanic corrosion.

Referring now to FIG. 4, a schematic diagram of the corrosion sensor 100 in a configuration to detect galvanic corrosion is illustrated. In FIG. 4, the cover 102 is shown in partial cutaway. It can be appreciated from FIG. 4 that the cover 102 covers substantially all of sensor 100 except for the corrosion sensitive connector 108. In the embodiment of FIG. 4, the corrosion sensitive connector 108 is further provided with a conduction lead 402. The conduction lead 402 may be comprised of steel, zinc, or other metals or alloys thereof. The conduction lead 402 may connect to a test object 404. In this way, the sensor 100 may be better equipped to detect galvanic corrosion as is known to occur in certain applications. The test object 404 could be a portion of a ship, an aircraft, a tank, a pipeline, or any number of test objects for which corrosion monitoring is desired.

Figure 5:
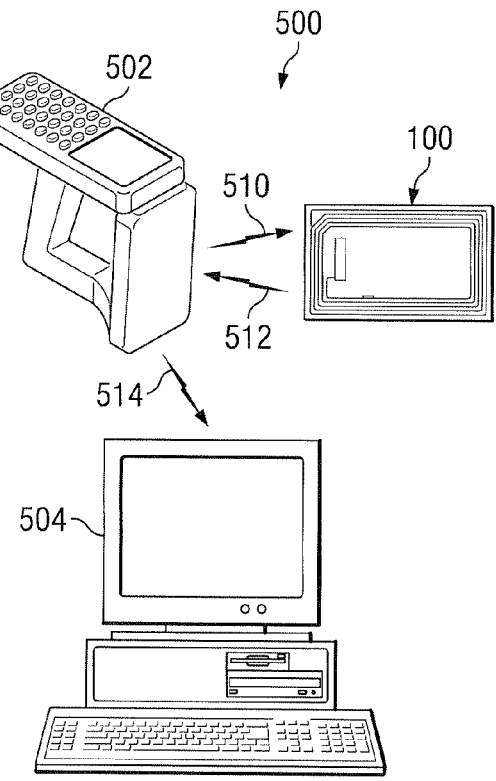
FIG. 5 is a diagram of one embodiment of a system for monitoring corrosion using wireless passive corrosion sensors according to the present disclosure.

Referring now to FIG. 5, one embodiment of a system for monitoring corrosion using wireless passive corrosion sensors according to the present disclosure is shown. In the present embodiment, the system 500 comprises a scanner 502, together with a number of corrosion sensors 100. It will be appreciated that although only a single sensor 100 is shown, a typical system would have a number of sensors 100. Furthermore, the sensors could be in any configuration, including the sensor 100 as shown. The sensors could also be configured as in FIG. 3 or as in FIG. 4.

The reader or scanner 502 will transmit microwave, magnetic, or radiofrequency energy 510 to the sensor 100. The reader 502 may be a handheld reader or could be stationary and capable of reading multiple sensors 100 simultaneously. Some embodiments of the system 500 will be based upon load modulation or reflected power/backscatter technology. One commercially available device that may be utilized as the scanner 502 in certain embodiments is the Texas Instruments RFID Systems S4100 Multi-Function Reader available from Texas Instruments Incorporated of Dallas, Tex.

There may be a separate transmission of an interrogator signal 510 from the scanner 502 and a separate response signal 512 from the sensor 100. In some embodiments, both the scanner 502 and the corrosion sensor 100 will have a single antenna that is used for both transmission and reception. The scanner 502 and sensor 100 may operate in accordance with known standards, such as the ISO/IEC 18000 RFID Air Interface Standard. Other embodiments may operate according to other standards or according to a custom-designed interface.

Passive RFID tags or sensors of the present disclosure that operate at frequencies below 100 MHz are typically powered by magnetic induction. An alternating current in a scanner 502 coil induces a current in the sensor 100 antenna coil 104. This allows charge to be stored in a capacitor that may then be used to power the electronics of the sensor 100. When the sensor 100 has been powered, the information contained within the sensor 100 may be sent back to the scanner 502 by a process called load modulation. In load modulation, the loading of the sensor's coil is changed in a pattern over time that affects the current being drawn by the scanner coil. In order to recover the information or identity transmitted by the sensor 100, the scanner 502 decodes the change in current as a varying potential developed across a series of internal resistors (not shown).

Because the sensors 100 may be located some distance from the scanner 502, possibly buried with the pipeline or imbedded in the structure of the test object, data coupling between the scanner 502 and the sensor 100 may only occur where the magnetic field between the scanner 502 and the sensor 100 is strong enough to allow. This communication region may be known as the near field region. Beyond the near field region, the far field region is where energy from the scanner 502 begins to propagate as radio waves.

The boundary of the near field and far field is governed by the frequency of the alternating current used to energize the coils of the scanner 502. The boundary is approximately limited to a distance of $C/2\pi f$, where C equals the speed of light and f equals the frequency. In one embodiment, 13.56 MHz sensors will be used which will limit interaction distance to approximately a maximum of 11.7 feet. The magnetic field strength between the scanner 502 and the sensor 100 falls off in proportion to $1/D^3$, where D is the distance from the scanner 502 to the sensor 100. Depending upon the location of the sensor 100 and/or the test object, larger scanners 502 and/or sensors 100 could be utilized to increase the effective communication distance.

Higher frequency systems have a relatively short range in the near field and therefore a different capture principal may be utilized. An electromagnetic capture method may be used to read sensors 100 operating at frequencies above about 100 MHz. This technique involves the use of electromagnetic waves propagating from the scanner 502 to power the sensor 100 in the far field region. Using this technique, data cannot be sent back to the reader using load modulation because the sensor 100 is operating beyond the near field. In such an embodiment, radio frequency backscatter may be used.

The sensor 100 electronics may alter the impedance of the antenna 104 and thereby reflect back some of the incident RF energy to the scanner 502. In this embodiment, the scanner 502 uses a sensitive receiver to attain the identification or other information from the sensor 100 utilizing the pattern of reflections that is coded as variation in the amplitude of the received signal 512. In this embodiment, the energy delivered to the sensor 100 from the scanner 502 will follow an inverse square law. The return signal 510 will also follow an inverse square law. Thus, the transmit power is attenuated by a $1/D^4$ law. Although this is a very rapid decline in signal strength over distance, the system 500 may work over a distance of about 3 to 4 meters, or in some cases even further.

Theoretically, the sensors 100 can operate on virtually any frequency, but in practice they may be limited by varying regulations to one of a number of specified bands. The band utilized may be selected based upon the end use of the sensor 100. Between about 100 and 500 kHz, the signal will have good penetrative properties for buildings and may also work around conductive barriers such as liquids and other materials. However, a low reading speed may be limiting at this frequency. The frequency band between about 10 and 15 MHz has a medium reading speed, but may not be able to penetrate sufficiently to reach the desired test object. Even higher frequencies than these may be utilized and may achieve long range reading capabilities when limited only by line of sight. However, the higher frequencies are more easily thwarted by obstructions such as walls, soil, water, etc. Moreover, the higher band frequencies may be prone to problems with reflection and interference.

In light of the various limitations with regard to the frequency bands, the low and high bands may be most useful for underground monitoring. However, the higher frequency bands may be useful for galvanic type sensors placed on above ground portions of a test object. In one embodiment, a frequency of about 126 kHz may be utilized. This frequency is virtually transparent to soil, concrete, paper, water, conductive liquids and slurries. The sensors 100 and scanner 502 may also have anti-collision circuitry and/or software such that multiple sensors 100 can be scanned simultaneously with a single scanner 502.

The sensor 100 may be visible or may be covered or hidden within the structure or test object being monitored. In any event, the sensor 100 receives the wireless energy 510 and responds with the confirmation signal 512. The confirmation signal 512 may be received and stored by the reader 502. It can be appreciated that data from many sensors 100 may be read and stored within the reader 502. As described, in some embodiments each sensor 100 may be able to respond with a unique ID number and possibly other information concerning the location, placement, or state of the sensor 100.

In some embodiments the system 500 will also have a computer 504. This computer could be a laptop, a personal computer, a server, a workstation, or a simply a data repository. The reader 502 may communicate with the computer 504 the information 514 obtained from scanning for the sensors 100. In this manner, data may be correlated using the computer 504. Data 514 could be communicated between the computer 504 and scanner 502 via wire or wirelessly according to known protocols. In some embodiments, a number of scanners 502 could be used, possibly by multiple persons, when scanning a very large object. The data could be correlated and condensed by the computer 504 such that a complete picture of the state of corrosion of the test object can be constructed.

Figure 6:
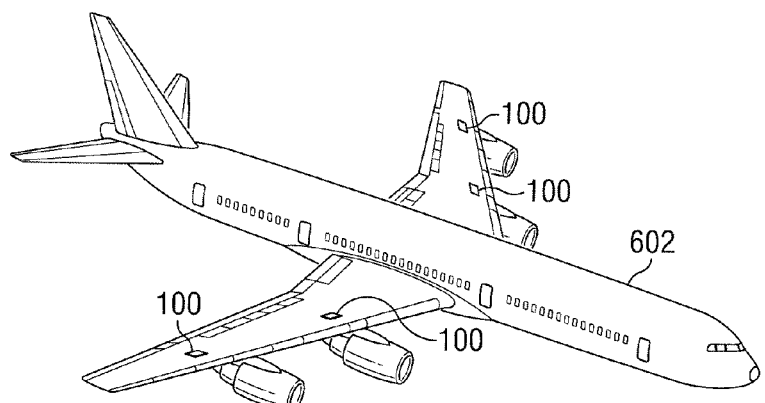
FIG. 6 is an illustration of one possible placement of wireless passive corrosion sensors on a test object.

Referring now to FIG. 6, one possible application of the corrosion sensors 100 on a test object 602 is shown. In the embodiment of FIG. 6, a test object 602 is an aircraft. As described, the test object 602 could be any number of structures or locations where corrosion is being monitored. Here, four sensors 100 are shown at various locations on the test object 602. As has been described, these corrosion sensors 100 may be scanned and their locations recorded.

Figure 7:
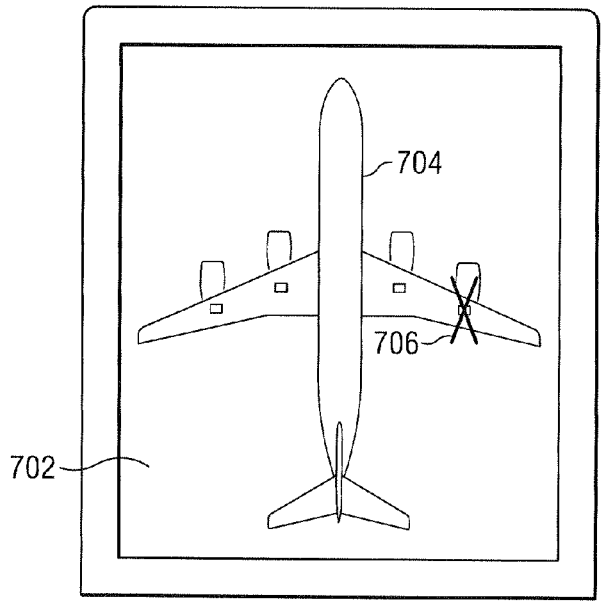
FIG. 7 is a graphical display of a test object being monitored for corrosion.

Referring now to FIG. 7, a graphical display of an object being monitored for corrosion is shown. A display 702 could be located on the hand-held scanner 502, the computer 504, or on another suitable location. A graphical representation or model 704 may be constructed based upon the test object 602. In some embodiments, the model 704 may be three dimensional such that a user could visually determine the state of corrosion of the entire test object 602. In FIG. 7, a point of corrosion 706 is illustrated graphically on the model 704. This may correspond to corrosion detected by one of the corrosion sensors 100 shown in FIG. 6. In addition to the location of the corrosion 706, the display 702 could also provide information obtained from the relevant corrosion sensor. As described, this may include the exact location of the corrosion sensor within the test object, as well as the date of installation of the corrosion sensor and other pertinent information. It can be that the corrosion sensors and monitoring described herein provide a relatively quick way to scan a test object 602 for corrosion without dismantling the test object 602. In some cases, the test object 602 may be immediately decommissioned based upon the readings obtained from the corrosion sensors. In other embodiments, all or a portion of the test object 602 could be flagged for further corrosion or structural testing.

Figure 8:
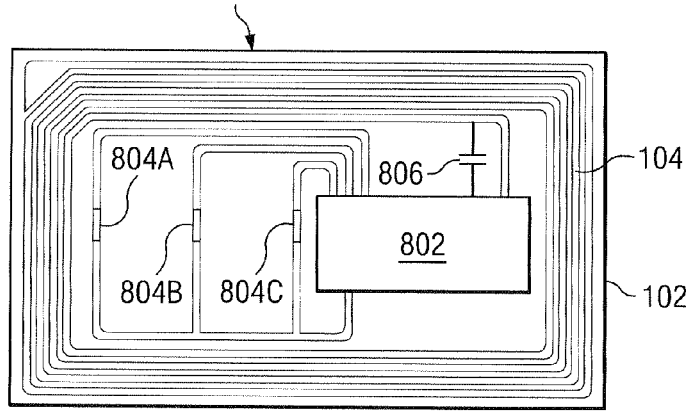
FIG. 8 is another embodiment of a wireless corrosion sensor according to aspects of the present disclosure.

Referring now to FIG. 8, another embodiment of a wireless corrosion sensor according to aspects of the present disclosure is shown. The sensor 800 is similar in some aspects to the sensors previously described, such as the sensor 100 of FIG. 1. The sensor 800 has a covering shown here with the top half removed to illustrate the internals of the sensor 800. An antenna 104 is provided which, once again, is utilized by the sensor 800 to receive power or an interrogation signal as well as provide any return signal.

The sensor 800 provides a microchip 802 that may be connected to a number of corrosion sensitive connectors. In the present embodiment, three such connectors are illustrated: 804a, 804b, and 804c. The chip 802 may be a custom made complimentary metal oxide semiconductor (CMOS) chip or another chip that is capable of performing the requisite functionality, as will be described herein. The overall design of the sensor 800 is such that varying degrees of corrosion may be detected by the sensor 800. This may be accomplished in a number of way, such as by each of the corrosion sensitive connectors 804a, 804b, 804c having a different thickness. In another embodiment, each of the connectors 804a, 804b, 804c may be comprised of a slightly different material. Making the connectors 804a, 804b, 804c of different material may also allow for the detection of different types of corrosion. Corrosion by the presence of multiple different chemicals of corrosive agents could be tested utilizing the sensor 800.

When the sensor 800 is energized or activated by a scanner, the chip 802 may provide a test current into each of the corrosion sensitive connectors 804a, 804b, 804c. It can be seen that the corrosion sensitive connectors 804a, 804b, 804c are arranged in parallel in the present embodiment (though they may share a power lead). The chip 802 determines whether the circuit is completed through each of the corrosion sensitive connectors 804a, 804b, 804c (or has a substantial degree of continuity therethrough). The chip 802 may then encode the results of the test of the corrosion sensitive connectors 804a, 804b, 804c and transmit the results on the antenna 104.

In one embodiment, the corrosion sensitive connectors 804a, 804b, 804c will be connected to an input/output I/O port on the chip 802. A positive voltage can be applied to each of the corrosion sensitive connectors 804a, 804b, 804c and the voltage on the connectors read by the I/O port. In one logic mode, the port would read a '1' for each intact connector. In the present embodiment with three corrosion sensitive connectors 804a, 804b, 804c if the connectors are attached to the least significant bits of a four bit port, and each is intact, the result read into the chip 802 would be '0111'. If the first sensor was substantially corroded the input would become '0110', and if the first two connectors were corroded the input would become '0100'. It can be appreciated that other schemes are possible including attaching many more connectors on the same chip 802 and sensor 800.

In FIG. 8, the capacitor 806 that may be needed to store power to operate the CMOS chip 802 is shown in one of many possible locations. It is also understood that in other embodiments, the capacitor 806 could be an integral part of the antenna 104, the chip 802, or otherwise located elsewhere on the sensor 800. It is also understood that in a production version of the sensor 800, the cover 102 will cover substantially all of the components of the sensor 800. The corrosion sensitive connectors 804a, 804b, and 804c may be exposed to the ambient environment to detect corrosion.

Utilizing a sensor 800 as shown in FIG. 8, or possibly a plurality of sensors as previously described (each with a different corrosion sensitive connector material or thickness) degrees of corrosion may be effectively monitored. The composition and/or size of the corrosion sensitive connectors may be configured such that the sensor is activated at a number of different levels of corrosion. For example, trigger points could be set to activate when corrosion has occurred but is not serious, when corrosion is extensive, and when corrosion is severe. It may be useful to know when corrosion has occurred but is not serious for planning purposes or for testing purposes. Knowing that extensive corrosion has occurred may require scheduled repair and/or visual inspection. Severe corrosion may require immediate repairs and possibly abstaining from use of the monitored structure until inspection and/or repair can occur.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. An apparatus for monitoring a degree of corrosion comprising:
    an antenna that receives an interrogation signal;
    an integrated circuit powered by the interrogation signal from the antenna; and
    a plurality of corrosion sensitive connectors connected to the integrated circuit;
    wherein the integrated circuit in response to the interrogation signal provides a continuity test of each of the plurality of corrosion sensitive connectors and provides a response back through the antenna indicative of the continuity test results.

2. The apparatus of claim 1, wherein the plurality of corrosion sensitive connectors has corrosion sensitive connectors of at least two thicknesses.

3. The apparatus of claim 1, further comprising a capacitor for storing energy from the interrogation signal for use by the integrated circuit.

4. The apparatus of claim 1, wherein each of the plurality of corrosion sensitive connectors are connected to the integrated circuit in parallel.

5. An apparatus for monitoring a degree of corrosion comprising:
   an antenna that receives an interrogation signal;
   a digital circuit powered by the interrogation signal from the antenna; and
   a plurality of corrosion sensitive connectors connected to the integrated circuit;
   wherein the digital circuit in response to the interrogation signal provides a continuity test of each of the plurality of corrosion sensitive connectors and provides a digital response back through the antenna indicative of the continuity test results.

6. The apparatus of claim 5, wherein the digital circuit provides an identifier along with the continuity test results.

7. A method of modeling corrosion of a test object, the method comprising providing one or more wireless corrosion sensors, the each sensor comprising:
   a integrated circuit (IC) chip configured to provide a signal response when energized; and
   an antenna configured to wirelessly receive energy for energizing the circuit and to receive the signal response from the circuit and transmit the signal response; and
   a plurality of corrosion sensitive connectors electrically connected to the IC chip to allow for continuity testing of each of the plurality of corrosion sensitive connectors;
   applying the plurality of corrosion sensors to the test object in locations where corrosion is monitored;
   wirelessly energizing the plurality of wireless corrosion sensors; and
   receiving a plurality of signal responses from the plurality of wireless corrosion sensors, the signal responses including results of continuity tests and an identifier from each of the corrosion sensors.

8. The method of claim 7, further comprising rendering a graphical depiction of a state of corrosion of the test object based upon the plurality of signal responses received from the plurality of wireless corrosion sensors.

* * * * *